United States Patent [19]

Grobbelaar

[11] 4,153,953
[45] May 15, 1979

[54] PROSTHETIC HIP JOINT

[76] Inventor: Charl J. Grobbelaar, Nedpark 1003, Trevenna St., Sunnyside, Pretoria, South Africa

[21] Appl. No.: 896,562

[22] Filed: Apr. 14, 1978

[51] Int. Cl.² .............................................. A61F 1/24
[52] U.S. Cl. ..................................... 3/1.913; 3/1.912; 128/92 CA
[58] Field of Search ........................ 3/1.9, 1.91, 1.912, 3/1.913; 128/92 C, 92 CA

[56] References Cited

U.S. PATENT DOCUMENTS

| | | | |
|---|---|---|---|
| 3,843,975 | 10/1974 | Tronzo | 3/1.913 |
| 3,848,273 | 11/1974 | Frey | 3/1.913 |
| 3,859,669 | 1/1975 | Shersher | 3/1.912 |
| 3,939,498 | 2/1976 | Lee et al. | 3/1.913 |
| 3,973,278 | 8/1976 | Shersher | 3/1.912 |

FOREIGN PATENT DOCUMENTS 1442990 7/1976 United Kingdom ..................... 3/1.913

*Primary Examiner*—Ronald L. Frinks

[57] ABSTRACT

A prosthesis according to the invention may be used in a hip joint operation by removing the femoral head and greater trochanter from a femur, forming a stem-receiving space in the interior of the femur, inserting the stem of the prosthesis into the space and cementing it in place and re-attaching the greater trochanter to the femur. The greater trochanter is re-attached by forming a pair of holes through the greater trochanter and, if necessary, through adjacent parts of the femur, inserting a U-bolt through the holes in the greater trochanter, the U-bolt passing through the hole in the stem, and pressing the greater trochanter against adjacent parts of the femur. This is done by screwing nuts along threaded limbs of the U-bolt to force clamping means against the trochanter and secure the trochanter in place.

12 Claims, 7 Drawing Figures

PROSTHETIC HIP JOINT

FIELD OF THE INVENTION

This invention relates to prosthetic joints and, in particular, to hip joints.

BACKGROUND OF THE INVENTION

In recent years, it has become practical to replace hip joints by prosthetic joints. This is done by removing the femoral head from a femur, forming a hole into the femur in a direction lengthwise of the femur, inserting into the hole a stem of a prosthesis and cementing the stem in place. A cup of suitable material, such as high density polyethylene, is located in the hip and the prosthesis has a ball which is located in the cup in an attempt to enable the prosthetic joint to simulate the action of a normal hip joint.

During the operation, the greater trochanter is removed from the femur and it is necessary to re-attach the greater trochanter once the prosthesis has been cemented in place. The greater trochanter must be securely located in place to allow bone union to occur and wire is normally used to tie the trochanter in position. However, it has been found that this is not always satisfactory as the wire sometimes slips or fractures.

It is therefore desirable to provide means making it possible to improve the effectiveness of these operations.

SUMMARY OF THE INVENTION

The present invention provides a prosthesis for a hip joint, comprising a head having a domed outer surface to be received in a suitable cup for pivotal movement in the cup, a relatively narrow neck extending from the head, and a stem extending from the neck for location in a femur, the stem containing a hole for receiving part of a means for attaching a greater trochanter to a femur.

In practice, the thickness of the stem will normally be less than its width along at least a major part of the length of the stem although the width may reduce gradually so that it is approximately equal to the thickness of the stem at that part of the stem which is furthest from the head. The width of the stem may initially increase as the stem extends away from the neck so that the likelihood of stem fracture in the region of the hole is minimal.

The prosthesis may include a U-bolt for passing through the hole and trochanter clamping means to be forced against a greater trochanter to locate the greater trochanter in place. Suitable nuts may be located on the U-bolt for forcing the clamping means against the greater trochanter. The clamping means may comprise trochanter clamps located on the limbs of the U-bolt. These clamps may have gripping claws for engaging the trochanter. For example, three claws may be provided on each clamp.

In order to minimize metal-to-metal contact within the femur, a sleeve may be provided for encircling the U-bolt in the region of the hole for preventing direct contact of the U-bolt with the stem.

In practice, the head, neck and stem will be formed from a single piece of metal and the U-bolt, clamping means and nuts will normally be made of the same material to minimize electrolytic action within the body. The parts of the prosthesis will all be made from a material which is physiologically acceptable and which will not corrode significantly within the body.

It has previously been proposed to have a part-spherical head with a diameter of about 22 mm connected to a neck with a minimum width of about 13 mm. However, the applicant has now discovered that a larger part-sperical head having a diameter which is at least twice the minimum width of the neck, and preferably in the region of 30 mm, can be arranged to sit deeper in the cup mounted in the hip and that this can reduce the dislocation rate and provide increased stability. Naturally, the minimum neck width will be suitably large to ensure that the likelihood of neck fracture is minimal and will therefore probably remain in the region of 13 mm.

The neck is preferably of circular cross-section and its diameter desirably increases progressively from a minimum diameter portion adjacent the head to a portion of greatest diameter in the region where the neck is connected to the stem. The minimum diameter portion of the neck may be joined to the head by a filleted portion to ensure that there are no sharp corners at the junction of the neck and the head. Similarly, the junction between the stem and neck may be filleted.

While the head and neck of the prosthesis may have highly polished surfaces, the stem may be sandblasted or otherwise treated to roughen it so that it can be readily cemented into a femur.

A prosthesis according to the invention may be used in a hip joint operation by removing the femoral head and greater trochanter from a femur, forming a stem-receiving space in the interior of the femur, inserting the stem of the prosthesis into the space and cementing it in place and re-attaching the greater trochanter to the femur, the greater trochanter being re-attached by forming a pair of holes through the greater trochanter and, if necessary, through adjacent parts of the femur, inserting a U-bolt through the holes in the greater trochanter, the U-bolt passing through the hole in the stem, and pressing the greater trochanter against adjacent parts of the femur by screwing nuts along threaded limbs of the U-bolt to force clamping means against the trochanter and secure the trochanter in place.

The clamping means may be positioned in any suitable position to offer the minimum possible resistance to muscle function. Once they have been located in place, the free ends of the limbs of the U-bolt may, if necessary, be cut off and the nuts may be fixed in position, for example, by damaging the threads on the limbs or in any other suitable manner. The head may then be inserted into a cup in the hip and, if necessary, means may be used to reduce the likelihood of the head leaving the cup.

BRIEF DESCRIPTION OF THE DRAWINGS

An embodiment of the invention will now be described, by way of example, with reference to the accompanying drawings, in which.

DETAILED DESCRIPTION OF THE DRAWINGS

Figure 1:
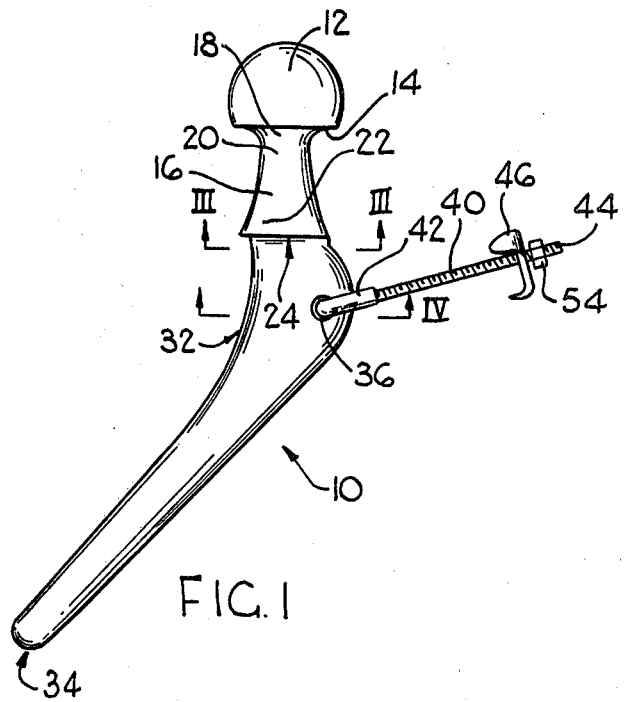
FIG. 1 is a side view of a prosthesis for a hip joint.
Figure 2:
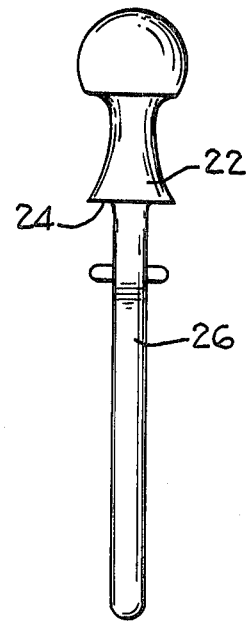
FIG. 2 is an end view of the prosthesis of FIG. 1.

As shown in the drawing, the prosthesis 10 has a part spherical head 12 having a flattened end portion 14 from which a neck 16 projects. The neck 16 has a filleted portion 18 integral with the head and extending into the minimum diameter portion 20 of the neck. The neck increases progressively in diameter towards a portion 22 of greatest diameter. As shown in FIG. 1, the neck has a continuously curved outline along its length.

Figure 3:
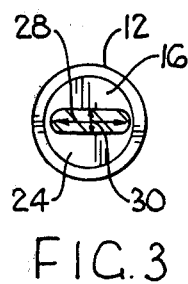
FIG. 3 is a cross-section through the prosthesis on the line III—III in FIG. 1.
Figure 4:
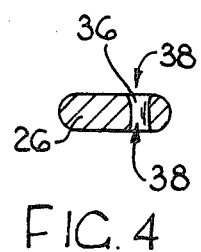
FIG. 4 is a cross-section through the stem of the prosthesis on the line IV—IV in FIG. 1.
Figure 5:
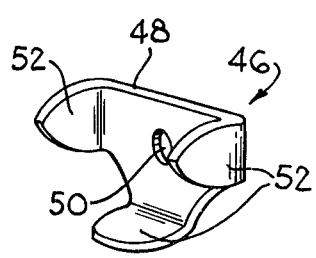
FIG. 5 is a schematic three-dimensional representation of a trochanter clamp forming part of the prosthesis.

From the greatest diameter portion 22 of the neck, the cross-section of the prosthesis reduces rapidly at a shoulder 24 and is united with a stem 26. As shown in FIG. 3, the stem has a width 28 which is substantially greater than the thickness 30 of the stem at a location adjacent to the shoulder 24. The thickness of the stem remains substantially constant along its length but the width increases to a maximum width at region 32 and then progressively decreases in width towards free end 34 of the stem. Towards the free end of the stem, the width of the stem is approximately equal to the thickness of the stem.

The prosthesis shown is formed of EN58J stainless steel having a carbon content not exceeding 0.05% (type 316). The head and neck have highly polished surfaces while the stem is roughened by sand-blasting. In the preferred form of the prosthesis, the head has a diameter of about 30 mm and the minimum diameter portion 20 of the neck 16 has a diameter of 13 mm. The stem sizes may vary slightly to allow for differently sized femurs. In practice, six different stem sizes should be adequate for most purposes.

The stem contains a hole 36 which has widened ends 38. A U-bolt 40 passes though the hole 36. The U-bolt is of a smaller diameter than the hole and, in the region of the stem, is encircled by an implantable silicone rubber tube 42 which prevents metal-to-metal contact between the U-bolt and the stem when the stem is implanted within a femur. The U-bolt has two threaded limbs 44 which are parallel to one another and which each carry a trochanter clamp 46.

Each trochanter clamp 46 has a plate 48 containing a hole 50 through which the respective limb passes and is provided with three claws 52 for engaging a greater trochanter. Nuts 54 are screwed onto the limbs 44 of the U-bolt for tightening the trochanter clamps against a greater trochanter.

The U-bolt 40, clamps 46 and nuts 54 are also made of EN58J stainless steel having a carbon content of less than 0.3%.

In a hip joint operation, a femoral head is sawn from a femur 56 at a location 58 and the trochanter 60 is sawn off from the femur 56 at location 62. A hole extending longitudinally of the femur 56 is then formed in the femur and the stem 26 of the prosthesis is surrounded with physiologically acceptable cement and inserted into the hole. The cement is used to bond the stem to the femur 56.

Figure 6:
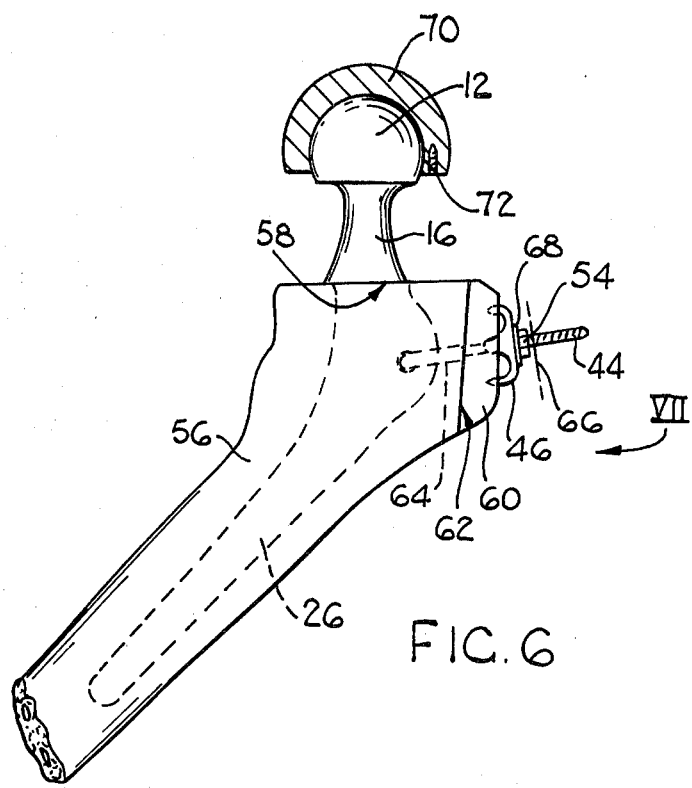
FIG. 6 is a schematic representation showing a femur provided with the prosthesis of FIG. 1.
Figure 7:
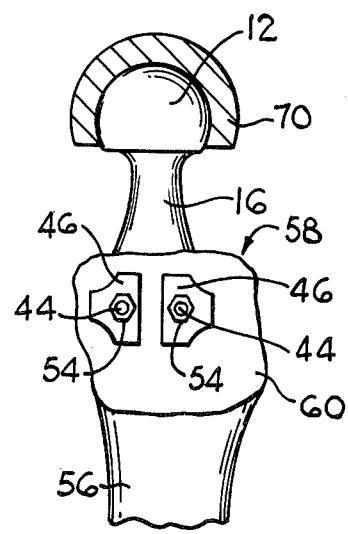
FIG. 7 is a view in the direction of arrow VII in FIG. 6.

The trochanter, and if necessary the femur, is drilled in the position shown in chain lines at 64 in FIG. 6 and the limbs 44 of the U-bolt 40 are passed through these holes. At this time, the U-bolt is, of course, located in the hole 36 in the stem. Once the greater trochanter 60 has been re-located at location 62, the trochanter clamps 46 are fitted onto the limbs 44 and the nuts 54 are screwed along the limbs to press the clamps against the greater trochanter, forcing the claws 52 into the greater trochanter. At this time, the clamps 46 are in the positions shown in FIG. 7. Once the greater trochanter is suitably secured in place, the limbs can be cut along the line 66 in FIG. 6 and the part of the U-bolt remaining attached to the stem 26 may be deformed to ensure that the nuts 54 will not inadvertently come loose.

In order to reduce the metal-to-metal contact between the nuts 54 and clamps 46, it is possible to insert suitable high density polyethylene washers 68 between the nuts and the clamps. Once the prosthesis has been attached to the femur in the manner shown, the head 12 of the prosthesis is inserted into a socket in the form of a high density polyethylene cup 70 located in the hip socket. The cup may include holes 72 (one of which is shown) into which the pin of the cup introducing instrument fits to permit accurate implantation into the acetabulum.

The head diameter of about 30 mm is considerably larger than that conventionally used but it has been found that the enlarged head size can give increased stability compared with smaller heads and can help to reduce the dislocation rate as the larger head can sit deeper in the cup 70.

I claim:

1. A prosthesis for a hip joint, said prosthesis comprising:
   a head having a domed outer surface to be received in a suitable cup in a hip for pivotal movement in the cup;
   a neck extending from the head;
   a stem extending from the neck for location in a femur;
   a hole in said stem;
   a U-shaped element for passing through the hole in said stem and through hole means in a greater trochanter;
   trochanter clamping means to be forced against the greater trochanter to secure the greater trochanter in place, and
   forcing means for location on the U-shaped element for forcing the clamping means against the greater trochanter;
   the head, neck and stem being formed from a single piece of metal and said piece of metal, U-shaped element, clamping means and forcing means all being made from material which is physiologically acceptable and which is resistant to corrosion within the body.

2. The prosthesis of claim 1, wherein the stem has a thickness which is substantialy constant along the major part of the length of the stem and has a width which is greater than the thickness of the stem along at least a major part of the stem and which reduces gradually over at least part of the length of the stem towards that part of the stem which is furthest from the head.

3. The prosthesis of claim 2, wherein the width of the stem initially increases as the stem extends away from the neck and towards the hole, providing a region of greatest width approximately in the vicinity of the hole whereby likelihood of stem fracture in the region of the hole is reduced.

4. The prosthesis of claim 3, wherein said U-shaped element has spaced parallel limbs and said clamping means comprises trochanter clamps located on said limbs, said clamps having gripping claws for engaging and penetrating a greater trochanter for securing said greater trochanter.

5. The prosthesis of claim 3, wherein an implantable sleeve is provided for encircling the U-shaped element in the region of the hole for preventing direct contact of the element with the stem.

6. The prosthesis of claim 3, wherein said head is a part-spherical head having a diameter which is at least twice the minimum width of the neck.

7. The prosthesis of claim 6, wherein said diameter of the head is in the region of 30 mm and said neck has a minimum diameter which is in the region of 13 mm.

8. The prosthesis of claim 6, wherein the neck is of circular cross-section and has a diameter which increases progressively from a minimum diameter portion adjacent the head to a portion of greatest diameter in the region where the neck is connected to the stem, said minimum diameter portion being joined to the head by a filleted portion.

9. A prosthesis for a hip joint, said prosthesis comprising:
- a head having a suitably smooth, polished part-spherical outer surface to be received pivotably in a cup mounted in a hip for replacing a femoral head;
- a neck integral with said head and having a minimum diameter portion with a diameter less than half of the diameter of said outer surface for supporting said head at a location spaced from a femur;
- a stem integral with said neck at the opposite end of said neck to said head and implantable in a femur, said stem initially increasing in width as it extends away from said neck to a portion of greatest width and thereafter reducing in width, said stem having a relatively coarse outer surface and being bondable in a femur by a physiologically acceptable cement;
- a hole in said stem approximately at said portion of greatest width, said stem having an edge that is to be located closest to a greater trochanter when said stem is implanted in a femur and said hole being located closest to said edge;
- a U-bolt for passing through said hole and having substantially parallel limbs for passing through hole means in a greater trochanter, said limbs being threaded over at least part of their length;
- trochanter clamping means for mounting on said limbs and engaging a greater trochanter for pressing a greater trochanter towards a femur in which said stem is implanted; and
- nut means for threaded engagement with said limbs for forcing said clamping means against a greater trochanter, said head, neck and stem being formed from a single piece of metal and said U-bolt, clamping means and nut means being formed of substantially identical metal for minimizing electrolytic action thereof within the body, said metal being physiologically acceptable and essentially non-corrosive in the body.

10. The prosthesis of claim 9, further comprising an implantable sleeve for encircling said U-bolt in the region of said hole for preventing metal-to-metal contact between said U-bolt and said stem.

11. The prosthesis of claim 10, wherein said trochanter clamping means comprises trochanter clamps located one on each limb of said U-bolt, said trochanter clamps each having a plurality of claw means to be forced into a greater trochanter for locating said trochanter clamps positively with respect to a greater trochanter.

12. A prosthesis for a hip joint, comprising a head having a smooth domed outer surface to be received in a suitable cup located in a hip socket for pivotal movement in the cup,
- a neck extending from the head, said neck being of circular cross-section and having a diameter increasing progressively from a minimum diameter portion adjacent the head to a portion of greater diameter adjacent a shoulder for resting against a femur, said minimum diameter portion of the neck being joined to the head by a filleted portion,
- a stem for location in a femur, said stem extending from said shoulder and having a substantially constant thickness along essentially all of its length and a width which is greater than said thickness along at least a major part of its length, said width initially increasing as the stem extends away from the neck to a region of greatest width and thereafter reducing gradually so that it is approximately equal to the thickness of the stem at a part of the stem which is furthest from the head, and
- a hole formed in the stem approximately in the region of greatest width for receiving part of a means for attaching a greater trochanter to a femur,
- said head, neck and stem being formed from a single piece of material which is physiologically acceptable and which is resistant to corrosion within the body and said head being a part-spherical head having a diameter which is at least twice the minimum diameter of the neck.

* * * * *